May 7, 1940. G. C. THOMAS, JR Plant Pat. 393
ROSE
Filed May 25, 1939
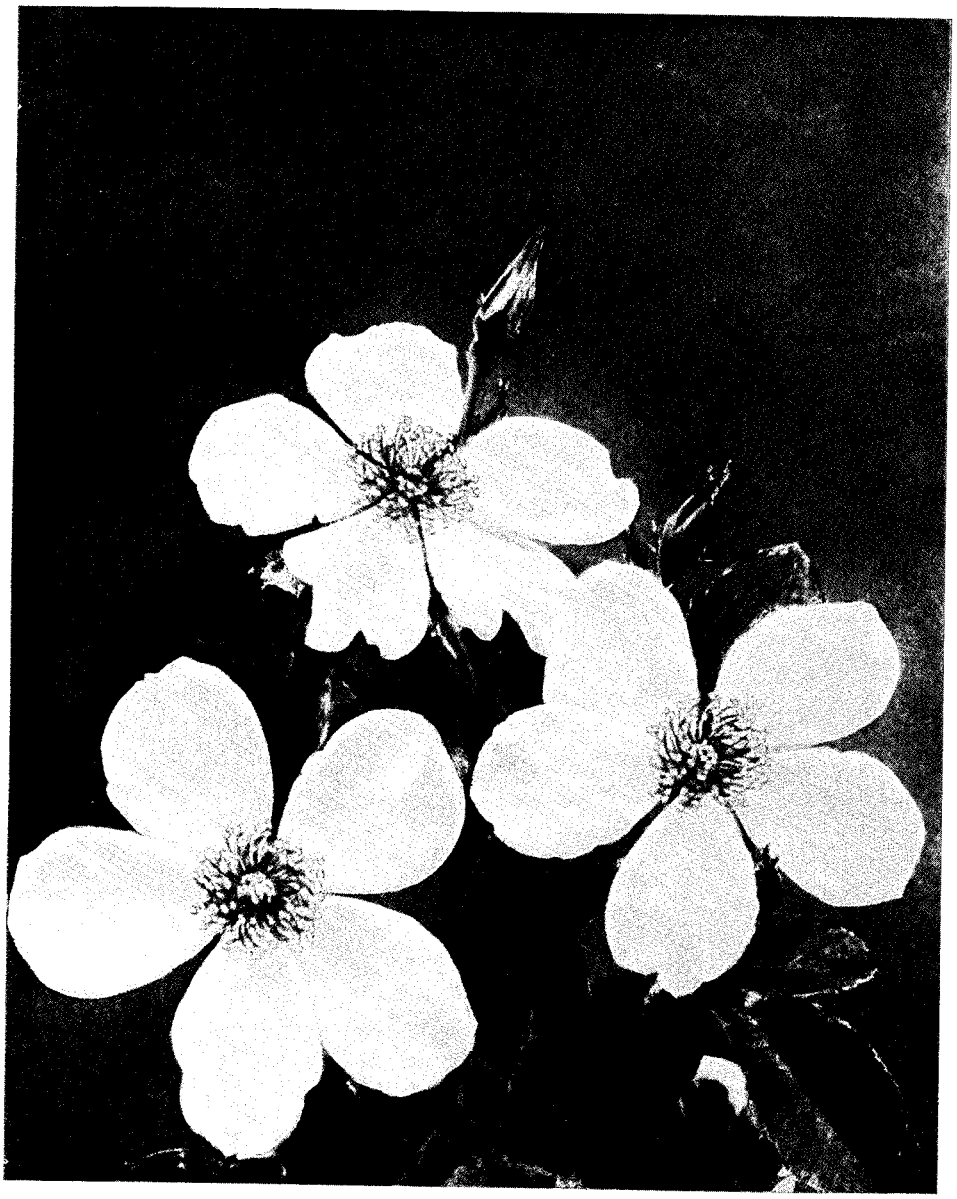
INVENTOR
George C Thomas Jr. Dec'd By
Josephine Moorhead Thomas Gardner &
George C Thomas III, Executors
By Orville M. Kile
PLANT PATENT AGENT Patented May 7, 1940

Plant Pat. 393

UNITED STATES PATENT OFFICE

393

ROSE

George C. Thomas, Jr., deceased, late of Beverly Hills, Calif., by Josephine Moorhead Thomas Gardner and George C. Thomas, 3rd, executors, Beverly Hills, Calif., assignors to Armstrong Nurseries, Ontario, Calif.

Application May 25, 1939, Serial No. 275,758

1 Claim. (Cl. 47—61)

This new variety belongs to the hybrid tea class and is the result of definite breeding efforts carried on by the inventor. It was produced from the seed contained in a seedpod which had resulted from crossing the two roses Attraction and Bloomfield Completeness, the latter being the seed parent. It has been reproduced asexually by budding and its characteristics have been retained.

The most important characteristics of this rose which in combination distinguish it from all other varieties are: (1) its habit of producing blooms throughout eight or nine months of the year, at least in mild climates such as that in Southern California; (2) its glossy, disease-proof, evergreen foliage which is persistent throughout the year in mild climates such as that of Southern California; (3) its single, five-petaled, large, yellow (gold to straw) flowers with purplish-wine stamens; and (4) its unusual vigorous climbing habit of growth.

The original illustration accompanying this application portrays, slightly enlarged and in approximately their true cool-weather colors, three specimens of the flowers of this new variety, together with some of the buds, leaves and stems.

Following is a detailed description of the flower and plant of this variety. Color plate references indicates Ridgway's Color Standards and Nomenclature. Where other colors are mentioned, the ordinary dictionary term is intended.

*The plant*

Growth: Where well grown, a very vigorous pillar type to ten feet or more; normally quite upright.

Blooming habit: Flowers produced in clusters at end of long, upright canes throughout the year in Southern California; individual flowers in cluster open successively rather than all at one time; each individual flower in cluster usually has long enough stem for cut flower use. Profuse bloomer.

Disease resistance: Disease-proof or nearly so.

Hardiness: Hardy at least to 20 degrees. Untested at lower temperatures.

Foliage: Abundant; medium size; thickly textured; glossy; medium green.

*Leaves.*—Average measurement 5 to 8 inches long; composed of 5 leaflets.

*Leaflets.*—1¾ to 2¼ inches long by 1 to 1¼ inches wide.

Sepals: Only very slightly foliaceous; extend some distance beyond unopened bud; usually entire and narrow lanceolate; outside pubescent; light Bice Green (Plate XVII) outside, approximately Absinthe Green (Plate XXXI) inside.

Stems: Strong, slender, straight and long, light Bice Green (Plate XVI) tinged with Vineceous Russet (Plate XXVIII).

*The flower*

Bud:

*Shape.*—Long-pointed.

*Size.*—Small to medium, measuring 1 to 1½ inches in length.

*Color.*—Lemon Yellow (Plate IV) to Empire Yellow (Plate IV).

*Peduncle.*—Covered with short hairs or pubescence, Bice Green (Plate XIII) to Cameo Brown (Pl. XXVIII).

Blossom:

*Size.*—Medium, usually 2½ to 3 inches in diameter when fully open.

*Form.*—Very flat when fully open.

*Petalage.*—Five petals of uniform shape and size.

*Petals.*—Shape—somewhat spatulate, with rounded top. Size—1 inch to 1½ inches long. Texture—substantial and of medium thickness. Appearance—glistening. Fragrance—slightly fragrant. Color—Empire Yellow (Plate IV) to Straw Yellow (Plate XVI) to Cream Color (Plate XVI) as the flower ages, varying with the weather. In cooler weather the color is a deeper yellow than in warm weather. Also the color of the flower lightens from the time it is in the bud stage until the petals drop. This lightening of the color is greater in warm weather than in cool weather. Behavior—petals last a moderate time then drop off cleanly.

*Reproductive organs.* — Pistils — many; bunched. Stigmas—Citron Yellow (Plate XVI). Styles—short; Citron Yellow tinged with Nopal Red (Plate I). Pollen—Cadmium Yellow (Plate III), Stamens—many, encircling bunched pistils. Filaments—uneven lengths; Vinaceous-Purple (Plate XXXVIII). Anthers—large; deep yellow, between Light Cadmium (Plate IV) and Aniline Yellow (Plate IV).

Having thus disclosed this invention, what is claimed is:

A new and useful variety of hybrid tea rose substantially as herein shown and described, characterized particularly by its everblooming habit; its heavy, glossy, disease-proof, evergreen foliage persistent throughout the year in mild climates; its vigorous climbing or pillar growth habit; and its single, five-petaled Empire Yellow to Cream Color blossoms with stamens of Vinaceous-Purple.

GEORGE C. THOMAS, 3RD.
JOSEPHINE MOORHEAD
THOMAS GARDNER.

*Executors of the Estate of George C. Thomas, Jr., deceased.*